US00PP27666P3

(12) United States Plant Patent
Fretwell

(10) Patent No.: US PP27,666 P3
(45) Date of Patent: Feb. 14, 2017

(54) ***CLEMATIS* PLANT NAMED 'BFCCFLA'**

(50) Latin Name: *Clematis lanuginosa×patens*
Varietal Denomination: BFCCFLA

(71) Applicant: Barry Fretwell, Exeter (GB)

(72) Inventor: Barry Fretwell, Exeter (GB)

( * ) Notice: Subject to any disclaimer, the term of this patent is extended or adjusted under 35 U.S.C. 154(b) by 63 days.

(21) Appl. No.: 14/545,362

(22) Filed: Apr. 27, 2015

(65) Prior Publication Data

US 2016/0316601 P1 Oct. 27, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

FOREIGN PATENT DOCUMENTS

QZ 2012 2785 2/2013

*Primary Examiner* — Keith Robinson
(74) *Attorney, Agent, or Firm* — Cassandra Bright

(57) ABSTRACT

A new and distinct *Clematis* hybrid named 'BFCCFLA' is disclosed, characterized by a distinctive ruffled, double or semi-double dark purple flowers. Plants have a dense, shrubby plant form and are well suited for container plantings. Flowers are produced from May/June through August/September. The new cultivar is a *Clematis* typically suited for ornamental container and landscape use.

1 Drawing Sheet

Latin name of the genus and species: *Clematis lanuginosa×patens*.

Variety denomination: 'BFCCFLA'.

BACKGROUND OF THE INVENTION

The new cultivar is the result of planned breeding program, conductor by the inventor, Barry Fretwell in Exeter, Great Britain. The seed parent is an unnamed, unpatented, proprietary *Clematis lanuginose*. The pollen parent is an unpatented, proprietary *Clematis patens* referred to as seedling number 3/9/6. The cross was made during 2005 and the selection of the new variety was made in 2007.

After selecting and isolating the new cultivar, asexual reproduction of the new cultivar 'BFCCFLA' was first performed in in Exeter, Great Britain at a nursery by vegetative cuttings in 2008. 'BFCCFLA' has since produced multiple generations, and has shown that the unique features of this cultivar are stable and reproduced true to type.

The inventor has applied for Plant Breeder's Rights protection in Europe during December 2012. The CPVO File Number is 2012/2785. Plants were not available to the public until May 10, 2104 by an offer for sale through F.M. Westphal Clematiskulturen, a company in Germany. The inventor confirms, the company Westphal received plant material directly from the inventor. The relationship between the inventor and Westphal is further documented on page 2 of the EU application, which names Westphal Clematiskulturen as the procedural representative for the inventor. As this first public sale originated from a source receiving material directly from the inventor, and occurred within one year of this filing, the inventor believes he has met the requirement of U.S.C. 102(b). A copy of the EU application is included with this application at the time of deposit. The EU application verifies on page 4 that at the time of filing in the EU, no sales had occurred.

SUMMARY OF THE INVENTION

The cultivar 'BFCCFLA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BFCCFLA.' These characteristics in combination distinguish 'BFCCFLA' as a new and distinct *Clematis* cultivar:

1. Double flowers, with a ruffled appearance.
2. Dark purple flowers
3. Flowering from May/June through August/September
4. Dense plant habit.
5. Suitability for container culture.

PARENTAL COMPARISON

Plants of the new cultivar 'BFCCFLA' are similar to the seed parent variety in most horticultural characteristics. However, the new variety differs from the seed parent in the following:

1. Different colored flowers.
2. Different flower type.

Plants of the new cultivar differ from the pollen parent in the following:

1. Different colored flowers.
2. Different flower type.
3. Shorter internode length.

COMMERCIAL COMPARISON

Plants of the new cultivar 'BFCCFLA' are similar to the commercial variety *Clematis* hybrid 'Patricia Ann Fretwell', unpatented, in most horticultural characteristics. However, the new variety differs from 'Patricia Ann Fretwell' in the following:

1. The new variety has a flower with a more open center.
2. The new variety has dark purple flowers, compared to pink flowers
3. Plants of the new variety are more vigorous.
4. The new variety has a different foliage shape.

The new variety can also be compared to *Clematis* hybrid 'Kiri Te Kanawa', unpatented, differing in the following characteristics:

1. The new variety has larger flowers.
2. The new variety has darker purple flowcrs
3. The new variety has flowers with more red-purple tones, whereas this comparator produces flowers in the violet-blue range.

BRIEF DESCRIPTION OF THE PHOTOGRAPH

The accompanying photograph in FIG. 1 illustrates in full color a typical mature flowers and foliage of 'BFCCFLA' grown outdoors in Germany. Age of the plant is approximately 8 months.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'BFCCFLA' plants grown outdoors in Germany. The growing temperature ranged from 0° C. to 25° C. at night to 0° C. to 30° C. during the day. No artificial light, photoperiodic treatments or chemical treatments were given to the plants. Plants were pinched twice. Measurements and numerical values represent averages of typical flowering types.

Botanical classification: *Clematis lanuginosa×patens* 'BFCCFLA'.

Age of the plant described: Approximately 8 months.

Container size of the plant described: Growing in the ground.

PROPAGATION

Typical method: Vegetative cuttings.

Time to initiate root developments: 25 days in the summer at 24° C.

Time to produce a rooted cutting/young plant: 50-60 days in the summer at 20° to 26° C.

Root description: Fine, fibrous.

PLANT

Growth habit: Shrubby climbing vine.

Time to produce a finished flowering plant: Approximately 12 to 14 months from an unrooted cutting to a deliverable plant, in a 1.5 of 2 Liter size container.

Height: Approximately 8 to 10 feet, measured from the soil line of the ground after approximately 8 months.

Plant spread: Approximately 2 to 3 feet.

Growth rate: Rapid during active growing season in Spring. 30 to 40 cm per month.

Branching characteristics: One main stem, easily making side branches from a pinch. Typically 2 to 4 main lateral branches form from a pinch.

Length of main stem: Approximately 200 to 300 cm.

Diameter of main stem: Approximately 0.3 cm.

Main stem color: Near RHS Green 143C, flushed with Greyed-Purple 185B.

Main stem texture: Glabrous.

Internode length: Varies from 5 to 13 cm.

Strength: Strong, flexible, semi-woody.

FOLIAGE

Leaf:

*Arrangement*.—Opposite, simple.

*Leaves per lateral branch*.—Average range 3.

*Average length*.—Approximately 5 to 8 cm.

*Average width*.—Approximately 4 to 5 cm.

*Shape of blade*.—Cordate.

*Apex*.—Acute.

*Base*.—Obtuse.

*Attachment*.—Stalked.

*Margin*.—Entire.

*Texture upper and lower surfaces*.—Glabrous.

*Color*.—Young foliage upper side: Near RHS Green 137A. Young foliage under side: Near RHS Green 137A. Mature foliage upper side: Near RHS Green 139A. Mature foliage under side: Near RHS Green 137A.

*Venation*.—Type: Pinnate. Venation color upper side: Near RHS Green 138B. Venation color under side: Near RHS Green 138A.

Petiole:

*Length*.—Approximately 6.0 to 8.0 cm.

*Diameter*.—Approximately 0.2 cm.

*Texture*.—Smooth.

*Color*.—Near RHS Green 143C, flushed with Greyed-Purple 185A.

FLOWER

Bloom period:

*Natural season*.—May/June through August/September.

Inflorescence type and habit: Double or semi-double, axillary. Solitary occurring, double-whorled or multi-whorled rotate flower. Flowers facing outward and slightly upward. Flowering occurs on both previous year's growth and current year's growth.

Quantity of flowers and buds on the plant at a given time: 20 to 50.

Rate of flower opening: Approximately 14 days from bud to fully opened flower.

Flower longevity on plant: Approximately 10 to 14 days, after fully opened. Self-cleaning.

Inflorescence size:

*Diameter*.—Approximately 10.0 to 14.0 cm.

*Depth*.—Approximately 6.0 cm.

Flowers:

*Corolla*.—Tepal arrangement: Multi-whorled, slightly upwardly cupped. Quantity: Typically 16 to 18 per flower. Size: Length: Approximately 7.0 cm. Width: Approximately 2.0 cm. Shape: Oblong. Margin:

Undulating, entire. Apex: Acute to short acuminate. Base: Blunt. Texture: Smooth, upper and lower surfaces.

*Color*.—Tepals: When opening: Upper surface: Near RHS Purple N77B. Lower surface: Near RHS Purple N77B. Fully opened: Upper surface: Near RHS Purple N79C and streaks near Purple N78A and Red-Purple 72A. Lower surface: Near RHS Purple 79B and 79C. Ageing: Upper surface: Near RHS Purple 79A and streaks near Red-Purple 60B62D. Lower surface: Near RHS Purple 79D.

Bud:

*Shape*.—Conical.

*Length*.—Approximately 4.0 cm.

*Diameter*.—Approximately 2.9 cm.

*Color*.—Near RHS Purple N79A streaked Greyed-Yellow 160A.

Peduncles:

*Length*.—Average range 8 to 12 cm.

*Width*.—Approximately 0.4 cm.

*Angle*.—Average 45°.

*Strength*.—Flexible.

*Color*.—Near RHS Yellow-Green 144B, flushed Purple N79A.

Fragrance: None.

REPRODUCTIVE ORGANS

Stamens:

*Number*.—Average 80 to 100 per flower.

*Stamen color*.—Near Yellow-White 158A.

*Stamen length*.—Average range 2.2 to 3.8 cm.

*Anther length*.—Approximately 0.08 to 0.12 cm.

*Anther color*.—Near RHS Orange-White 159A.

*Anther shape*.—Oblong.

*Pollen quantity*.—Moderate.

*Pollen color*.—Near Orange-White N159C.

Pistil:

*Pistil quantity*.—40 to 60 per flower.

*Length*.—Approximately 0.8 cm.

*Style length*.—Approximately 0.7 cm.

*Style color*.—Near RHS Yellow-White 158D.

*Stigma*.—Shape: Linear. Color: Near RHS Yellow-White 158D.

OTHER CHARACTERISTICS

Seeds and fruits: Not observed to date.

Disease/pest resistance: Neither resistance nor susceptibility to normal pests of *Clematis* has been observed. Better resistance for mildew diseases of *Clematis* has been observed. The most common known mildew pathogen is *Erysiphe aquilegiae*.

Temperature tolerance: Tolerates temperatures from approximately −25° C. to 45° C.

What is claimed is:

1. A new and distinct cultivar of *Clematis* hybrid plant named 'BFCCFLA' as herein illustrated and described.

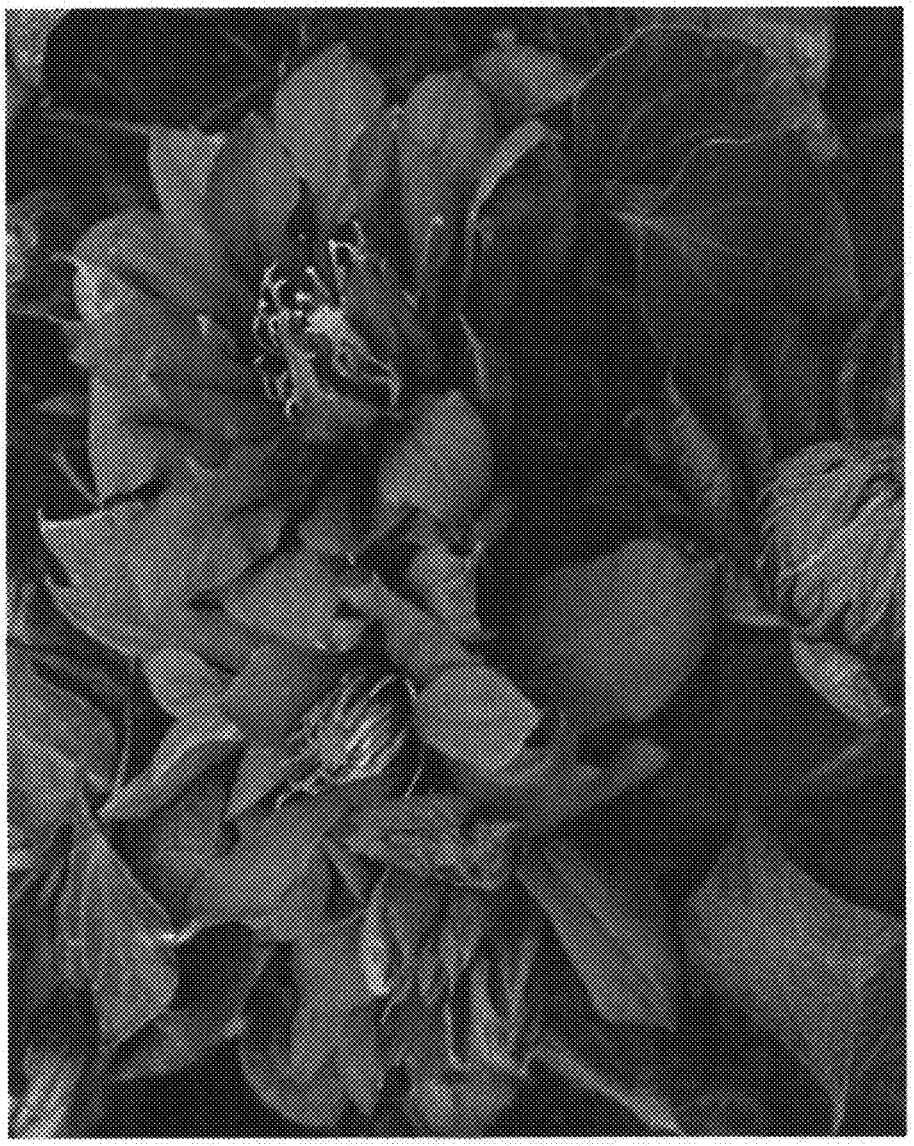

* * * * *